US007993822B2

(12) United States Patent
Chen et al.

(10) Patent No.: US 7,993,822 B2
(45) Date of Patent: Aug. 9, 2011

(54) AGING BIOMARKER

(75) Inventors: Cuiying Chen, Balegem (BE); Roland H. Contreras, Merelbeke (BE)

(73) Assignees: Vlaams Interuniversitair Instituut Voor Biotechnologie VZW, Ghent (BE); Universiteit Gent, Ghent (BE)

( * ) Notice: Subject to any disclaimer, the term of this patent is extended or adjusted under 35 U.S.C. 154(b) by 1037 days.

(21) Appl. No.: 11/792,203

(22) PCT Filed: Nov. 29, 2005

(86) PCT No.: PCT/EP2005/056299
§ 371 (c)(1),
(2), (4) Date: Aug. 6, 2007

(87) PCT Pub. No.: WO2006/058878
PCT Pub. Date: Jun. 8, 2006

(65) Prior Publication Data
US 2008/0003180 A1   Jan. 3, 2008

(30) Foreign Application Priority Data

Dec. 1, 2004   (EP) ..................................... 04106221

(51) Int. Cl.
*C12Q 1/00* (2006.01)
*G01N 33/48* (2006.01)
*G01N 33/00* (2006.01)
(52) U.S. Cl. ................................. 435/4; 436/63; 436/94
(58) Field of Classification Search .......................... None
See application file for complete search history.

(56) References Cited

U.S. PATENT DOCUMENTS

| 6,326,209 | B1 * | 12/2001 | Jia et al. ........................... 436/98 |
| 7,335,512 | B2 * | 2/2008 | Callewaert et al. .............. 436/94 |
| 2006/0014294 | A1 * | 1/2006 | Contreras et al. ............... 436/86 |

OTHER PUBLICATIONS

Shikata, Kohdoh et al. "Structural changes in the oligosaccharide moiety of human IgG with aging" 1998, Glycoconjugate Journal, vol. 15, 683-689.*
PCT International Search Report, PCT/EP2005/056299, dated Feb. 27, 2006.
Parekh et al., Age-Related Galactosylation of the N-linked Oligosaccharides of Human Serum IgG, J. Exp. Med., May 1988, pp. 1731-1736, vol. 167.
Grancinska et al., Abstract, Serum protein-bound carbohydrates in aging men and women, Klinische Wochenschrift, Nov. 1, 1977, pp. 1067-1069, vol. 55, No. 21.
Song et al., Abstract, Advanced glycation in D-galactose induced mouse aging model, Mech Ageing Dev. May 17, 1999, pp. 239-251, vol. 108, No. 3.
Sumar et al., Abstract, Analysis of glycosylation changes in IgG using lectins, Journal of Immunological Methods, Jul. 20, 1990, pp. 127-136, vol. 131, No. 1.

* cited by examiner

*Primary Examiner* — Jean Witz
*Assistant Examiner* — Charles Zoltan Constantine
(74) *Attorney, Agent, or Firm* — TraskBritt, P.C.

(57) ABSTRACT

The present invention relates to a marker that can be used as aging biomarker. More specifically, the present invention relates to the analysis of N-glycans in serum and its relation to the virtual age of the subject. This aging biomarker can be used to study the effect of medication, food compounds and/ or special diets on the wellness and virtual age of animals, including humans.

7 Claims, 13 Drawing Sheets

AGING BIOMARKER

The present invention relates to a marker that can be used as aging biomarker. More specifically, the present invention relates to the analysis of N-glycans in serum and its relation to the virtual age of the subject. This aging biomarker can be used to study the effect of medication, food compounds and/or special diets on the wellness and virtual age of animals, including humans.

Aging, a process involving multiple genes acting through complex pathways, is not yet fully understood in molecular and cellular terms. In humans, the aging process seems to be primarily under genetic control, and age-dependent diseases develop on this background as a consequence of other factors. Due to the rapidly increasing number of elderly people in many countries, there is a need for innovative treatments for age-related diseases. However, considering the low number of aging-related genes identified, a widely accepted model of aging has yet to be established. Therefore, in addition to studying aging mechanisms, the identification of candidate aging biomarkers to measure age-related changes may be of great value not only to gerontologists, but also to people in general, by preventing aging-related diseases through development of anti-aging medicines.

It is well known that the N-linked oligosaccharides of glycoproteins play important biological roles by influencing the functions of glycoproteins. They are important to initiation of various cellular recognition signals that are essential for the maintenance of the ordered social life of each cell within a multi-cellular organism. The sugar chains have characteristic features based on the structural multiplicity formed from a limited number of saccharide units. Although many studies reported the importance of the structural changes of glycans during development, little information is available on the changes in glycans during aging. Because the biosynthesis of glycans is not controlled by interaction with a template but depends on the concerted action of glycosyltransferases, the structures of glycans are much more variable than those of proteins and nucleic acids. Therefore, the structures of glycans can be easily altered by the physiological conditions of the cells. Accordingly, age-related alterations of the glycans are relevant to the understanding of the physiological changes found in aged individuals. It is important to determine the molecular events that occur in glycoconjugates during aging. Determination of the changes in the concentrations of N-glycan is fundamental to the discovery of valid biomarkers associated with biological processes such as aging and age-related diseases. Indeed, Robinson et al. (2003) disclosed a differential protein expression and glycosylation pattern in membrane proteins from premature aging Hutchinson-Gilford progeria syndrome fibroblasts. Shikata et al. (1998) showed that the N-glycosylation of IgG is age related, but only in female IgG samples. Notwithstanding these findings, there is still a need for a reliable and simple biomarker that can be used to evaluate aging, and the effect of diseases or compounds on the virtual age of a subject.

Surprisingly, we found that the serum concentrations of N-linked sugar structures changes during aging in human, mouse and rat and that N-glycan profiling could be used as an aging biomarker to predict the condition of human and animal health. These changes of N-linked sugar structures in serum are independent from the changes induced by IgG.

A first aspect of the invention is the use of the serum N-glycan profile as a biomarker for aging. In the general population the N-glycan profiles of serum samples with and without IgG evolve in a similar way. However, as it is known that the N-glycan profile of IgG is affected by diseases such as rheumatoid arthritis (Axford et al., 1992; Gornik et al., 1999). Therefore, in some cases, analysis of serum after removal of the IgG fraction may be preferred.

In this invention, we demonstrated that the serum N-glycan profile is species dependent, with age related peaks that are specific for a defined species. Therefore, another aspect of the invention is the use of agalacto N-glycans (peak 1: agalacto, core-α1,6-fucosylated biantennary and 2: bisected, agalacto, core-α-1,6-fucosylated biantennary) and galactosylated, fucosylated biantennary N-glycan (peak 6: bigalacto, core-α-1,6-fucosylated biantennary) as biomarker for aging in human Still another aspect of the invention is the use of serum N-glycan profile to test the effect of medication, food and/or diet on the virtual age of animals. Indeed, the N-glycan profile may be especially interesting to test the effect of dietary compounds and/or medication on the global health condition of an animal, including humans. The global health condition can be described then as a virtual age, as defined below. In a similar way, the N-glycan profile can be used to test the effect of chemical compounds on the global health conditions. Chemical compounds to be tested may be, as a non-limiting example, compounds that may be released in the environment, either deliberately, such as insecticides, fungicides or herbicides, or indirectly, such as solvents used in paintings.

Another aspect of the invention is a method for determining the virtual age of an animal, comprising a) obtaining a serum sample of said animal b) releasing the N-glycan fraction from the glycoproteins c) analyzing the N-glycan pattern and d) determining the virtual age according to selected N-glycans representative for the virtual age of the species. Preferably, the release of the N-glycan fraction is realized by a sialidase treatment and N-glycan samples are analysed using a DNA-sequencer.

DEFINITIONS

Aging as used here doesn't refer to the real age, but to the condition of the human of animal tested, and therefore the aging biomarker refers to a virtual age.

Virtual age: The virtual age of an animal (including humans) after a treatment is determined by comparing the N-glycan profile of the treated animal with a non-treated control group. As N-glycan profiles differ from species to species, representative age related peaks are defined for the animal species tested. For humans, age related peaks are the agalactoside N-glycans (peak 1 and 2) and the galactosylated, fucosylated biantennary fraction (peak 6). Using the age calibration curve of the representative peak or peaks of the non-treated animal, the virtual age of the treated animal can be determined.

Treatment as used here can be any treatment influencing age, such as, but not limited to, treatment with a chemical compound, influence of medication, food and/or diet. Supplying the compound or the medication can be in any way, including but not limited to oral supply, supply by inhalation, supply by injection or application on the skin.

BRIEF DESCRIPTION OF THE FIGURES

bi-β-1,4-galacto, core-α-1,6-fucosylated biantennary; Peak 7: bisected, bi-β-1,4-galacto, core-α-1,6-fucosylated biantennary; Peak 8: tri-β-1,4-galacto, 2,4-branched triantennary; Peak 9: trigalactos, branched fucosylated triantennary.

•: β-linked galactose; ○: p-linked GlcNAc; □: α-linked mannose; ■: β-linked mannose; Δ: α-1,6-linked fucose

EXAMPLES

Materials and Methods

Human Sera Samples

Healthy control samples were obtained from the Transfusion Center of the Red Cross in Ghent, Belgium, in accordance with Red Cross health standards (Negative for RA and WRN). A total of 100 blood samples were obtained from 10 female and 10 male donors for each age group (20, 30, 40, 50, 60 years).

Rheumatoid Arthritis Patients

Sera were obtained from 14 female patients (32 to 72 years) and 6 male patients (30 to 67 years) (see Table 1) with rheumatoid arthritis. All patients had been diagnosed by specialized clinicians in the Rheumatology Department of the University Hospital, Ghent.

Werner Syndrome

One serum sample from a 45 year old male with Werner syndrome was provided by Prof. Antonio Federico (Università degli Studi di Siena, Siena, Italy).

Animals and Blood Sampling

Female C57BL/6 mice were obtained from Iffa-Credo (Saint Germain-sur-l'Arbresle, France) at the age of 8-10 weeks. Hsp70.1−/− mice were bred as homozygotes in our facilities (Van Molle at al., 2002). Mice were kept in a temperature-controlled, air-conditioned animal house with 14-10 h light/dark cycles; they received food and water ad libitum.

Blood samples were obtained from the mice repeatedly at different ages. About 50-100 μl were obtained from each mouse from the retro-orbital plexus (behind the eye) with a capillary. The blood samples were left to clot for 30 min at 37° C., placed at 4° C. for at least 1 h, and then centrifuged for 10 min at maximum speed. The sera were removed and stored at −20° C.

Caloric Restrict Animals

Sera from mice and rats fed al libitum (AL) and a food restricted diet (CR) were purchased from the National Institution on Aging (NIA) (MD, USA). Sera from male BALB/c/AL and BALB/c/CR were obtained at age 12, 20, and 24 months, whereas sera from male F344/AL and F344/CR at age 18, 24, and 28 months. The animals fed ad libitum had free access to the diet (NIH-31; Purina Mill, Inc., Richmond, Ind.). The food restrict animals (CRs) were fed a special NIH-31 fortified formula, which was enriched with vitamins but 40% less calories as compared with the animal fed al libitum (Guo et al., 2002).

Purification of Immunoglobulin from Serum

The immunoglobulins were purified with the kit of ImmunoPure Immobilized Protein L (Pierce) by following the protocol supplement by the producer with slightly modification. A mixture of 10 μl of serum, 40 μl of Protein L and 130 μl of PBS was loaded on the membrane of Multiscreen-HV 96-well plate. Then washed eight times with 300 μl of PBS. The antibodies were eluted two times with 100 μl of 0.1 M glycine PH2 and were used for N-glycan analysis.

N-Glycan Analysis Using DNA-Sequencer

Processing of protein N-glycan samples had been described previously (Callewaert et al., 2001).

The glycoproteins were denatured by addition of at least 2 volumes RCM buffer (8 M urea, 360 mM Tris, pH 8.6, 3.2 mM EDTA) to each sample in a final volume of at least 50 μl, and the samples were then placed at 50° C. for 1 h. The N-linked glycans present on the serum proteins in 5 μl of serum were released after binding the protein to an Immobilon P-lined 96-well plate. They were then derivatized with APTS (Molecular Probes, Eugene, Calif., USA) and analyzed on an ABI 377A DNA sequencer (Applied Biosystems).

Data Analysis

Data analysis was performed using the Genescan 3.1.2 software (Applied Biosystems, Foster City, Calif., USA). We used the same fluorescence-overlap correction matrix that was used for DNA sequencing using BigDye dye terminators on our machine. Quantification analysis was carried out using SPSS 11.0 software.

Example 1

Glycomic Serum Profile from Human Sera

Figure 1:
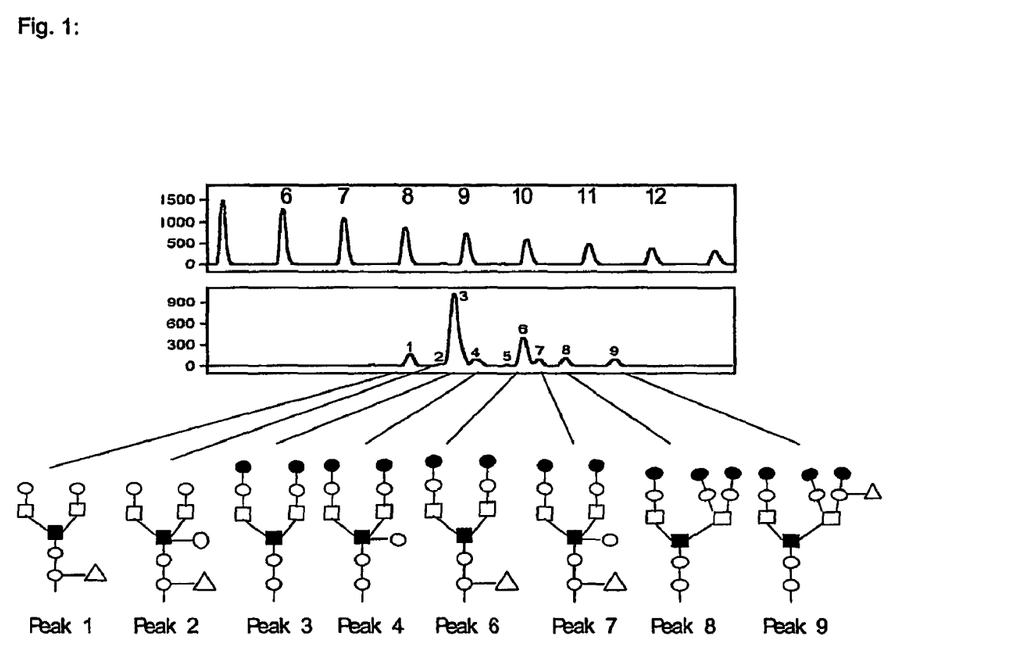
FIG. 1: N-glycan profile from total human serum. Nine peaks are clearly visible in the full detected range. The structure of the compounds represented by the peaks is indicated. Peak 1: agalacto, core-α-1,6-fucosylated biantennary; Peak 2: bisected, agalacto, core-α-1,6-fucosylated biantennary; Peak 3: bi-β-1,4-galacto, core-α-1,6-fucosylated biantennary; Peak 4: bisected bi-β-1,4-galacto, biantennary; Peak 6.
Figure 2:
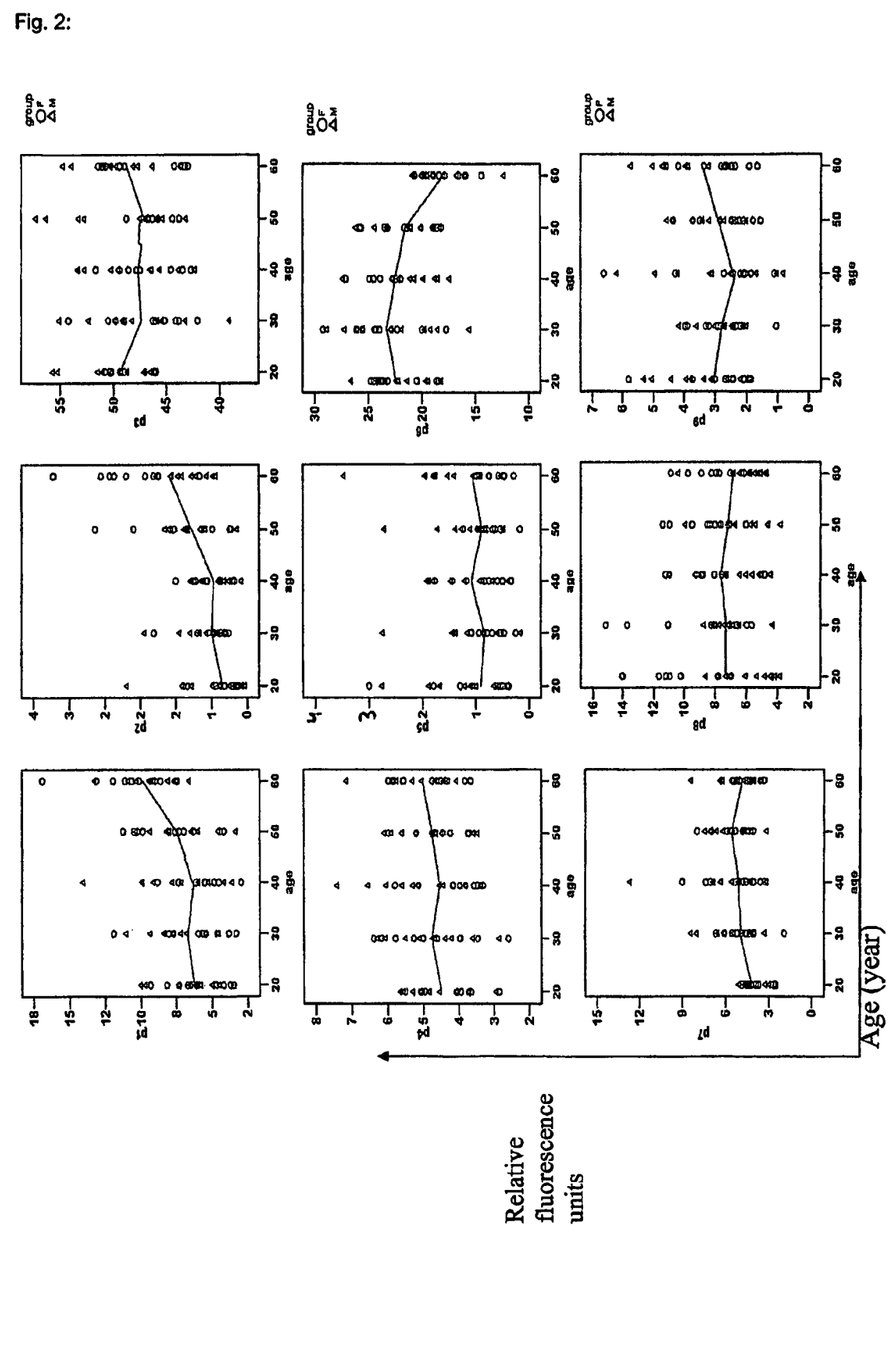
FIG. 2: Evolution of the N-glycan peaks in human serum in function of the age. The results are separately shown for male and subjects. Individual points are indicated, as well as the general trend.

This study used 100 human serum samples from five age groups (20, 30, 40, 50 and 60 years). Each age group consisted of 10 males and 10 females. N-glycan proteins were isolated and purified. The samples were digested with sialidase, and the N-glycan profiles of the different age and sex groups were analyzed by DSA-FACE. Quantification of the N-glycans was represented as peak heights of the 9 peaks (FIG. 1) that had been verified previously (Callewaert at al., 2004). The data were analyzed statistically by median and inter-quartile ranges for the 9 peaks over the 5 groups. The sizes of the peaks, representing the concentrations of the oligosaccharide structures, were examined statistically for evidence of correlation between N-glycans and aging. As shown in FIG. 2, the trend was for P1 and P2 to increase gradually with age, and for P6 to decrease. These three variables could be used as aging biomarkers to evaluate the state of health.

Figure 3:
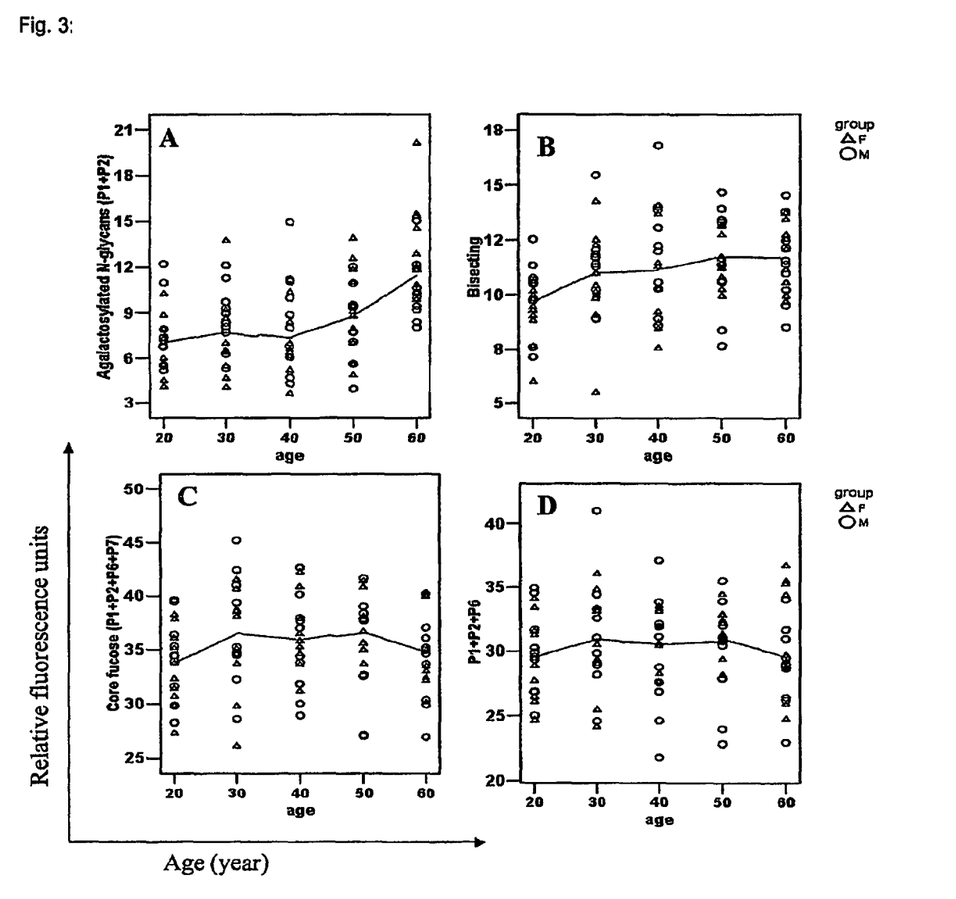
FIG. 3: The sum of the evolution of the N-glycan peaks in human serum in function of the age. A: total agalactosylated N-glycan: B: total bisecting N-glycan. C: total core fucosylated N-glycan. D: sum of Peak 1 and Peak 2.

To investigate the characteristics of a variable composed of the heights of peaks P1, P2, P6 and P7 for core fucose, of peaks P1 and P2 for agalactose, and P2 and P7 for bisecting GlcNAc residue, the peak heights were added (FIG. 3). The mean level of agalactosylated biantennary (P1 plus P2) and bisected GlcNAc residue was significantly increased (FIG. 3A, B), whereas the mean extent of core fucosylation remained unaltered (FIG. 3C). Moreover, the increased bisecting biantennary (P2+P4+P7) (FIG. 3C) was due to the Peak 2, as Peak 4 and 7 remained constant (FIG. 2).

Peak 1 is the biantennary, agalacto, core-α-1,6-fucosylated glycan. Its upregulation reflects of decreased galactosylated core-α-1,6-fucosylated biantennary (P6) as showed in FIG. 3D. Peak 2 represents the bisected, agalacto core-α-1,6-fucosylated structure. The increase of Peak 2 is a combination of undergalactosylation and increased bisected biantennary of the serum glycoproteins.

Example 2

N-Glycan Profiling of Human Antibodies

Figure 4:
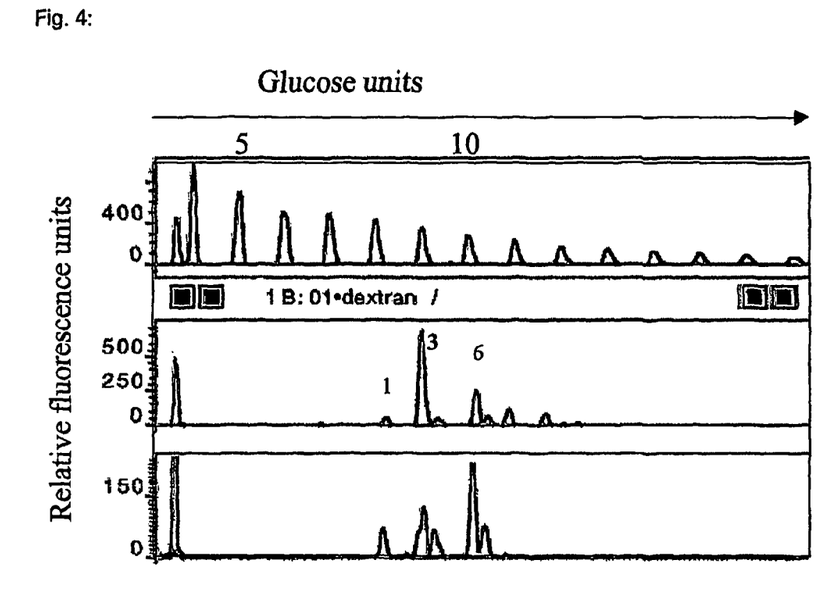
FIG. 4: N-glycan profile from serum without IgG and from IgG, indicating a different profile. Maltooligosaccharide reference (top), electropherogram of desialylated N-glycan derived from proteins in the serum without IgG (middle) and in the IgG (bottom).
Figure 5:
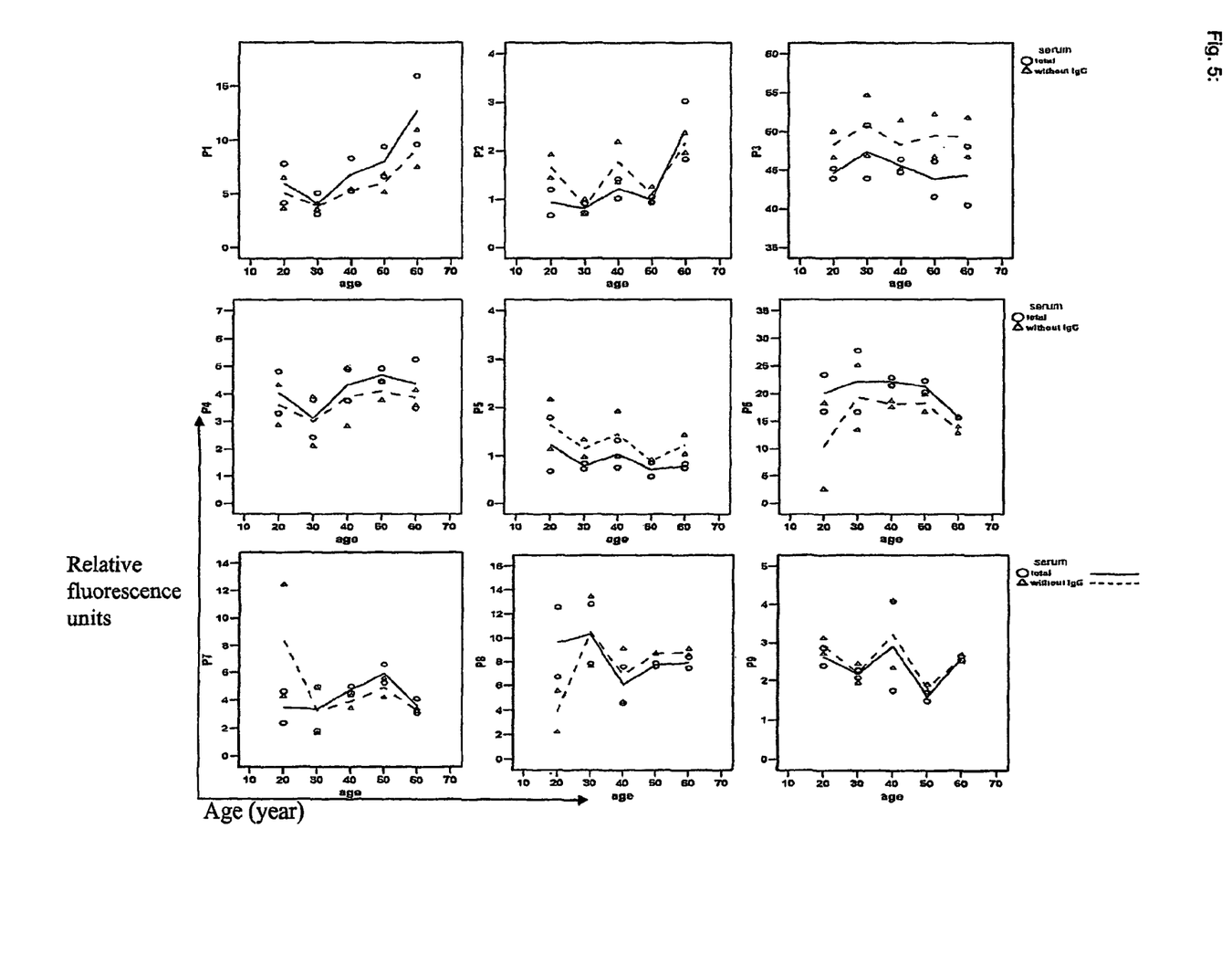
FIG. 5: Evolution of the N-glycan peaks in human serum without IgG and from IgG in function of the age.
Figure 6:
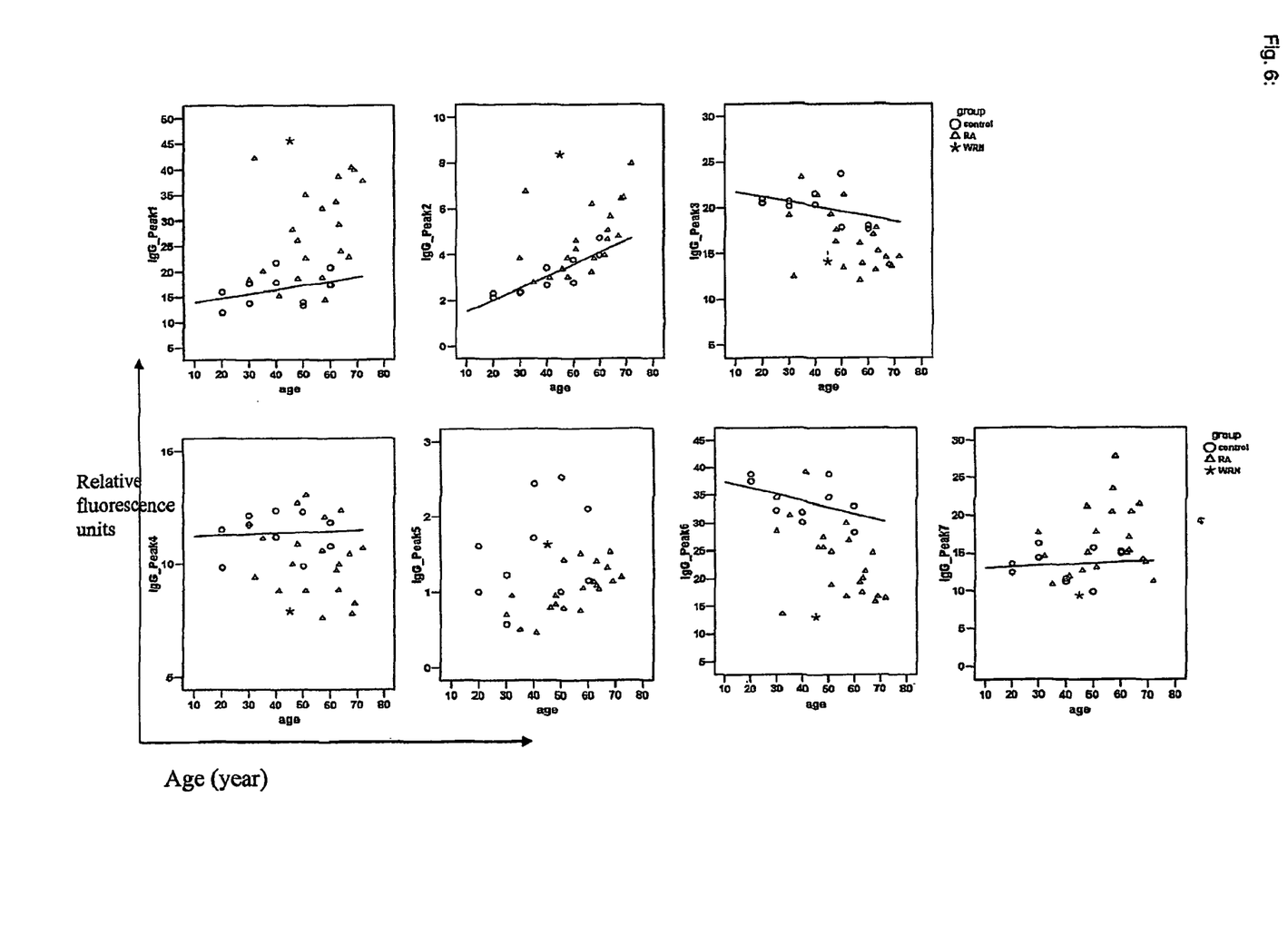
FIG. 6: Evolution of the N-glycan peaks in isolated IgG from humans in function of the age for rheumatoid arthritis patients (RA), Werner syndrome patients (WRN) and a male control group (CON). The line indicates the evolution in the control group.

Glycan proteins are key components of the immune system effectors. The sugar structures attached to immunoglobulins are important in the synthesis, stability, recognition and regulation of these proteins, and in many of their diverse interactions. To evaluate changes in the concentration of N-glycans during the aging process, we examined the N-glycan profiles of immunoglobulin, and of serum depleted of immunoglobulin. The antibodies were purified using Protein L agarose, which binds Ig (see M&M). N-glycan profiling was performed by DSA-FACE and shown in FIG. 4. Although N-glycan profiles are tissue specific, the seven sugar structures were present in both serum and immunoglobulin. In agreement with previous reports, the major N-glycan structure attached to antibodies is fucosylated bi-galactosylated biantennary (P6), whereas bi-galactosylated biantennary (P3) is most abundant in total serum (FIGS. 1 and 4). As shown in FIG. 5, the sizes of the peaks in total serum and in serum without antibodies were similar. This indicates that the relative concentration of sugar structures in the total serum is not altered by that of the antibodies. Interestingly, the glycan profile of antibodies was similar to that of total serum in displaying increases in P1 and P2 and a decrease in P6. In addition, the decrease abundance of P3 was evidenced only in the IgG but not in the total serum or serum without IgG (FIG. 6).

Example 3

N-Glycan Profiling in Rheumatoid Arthritis (RA) Patients

Figure 7:
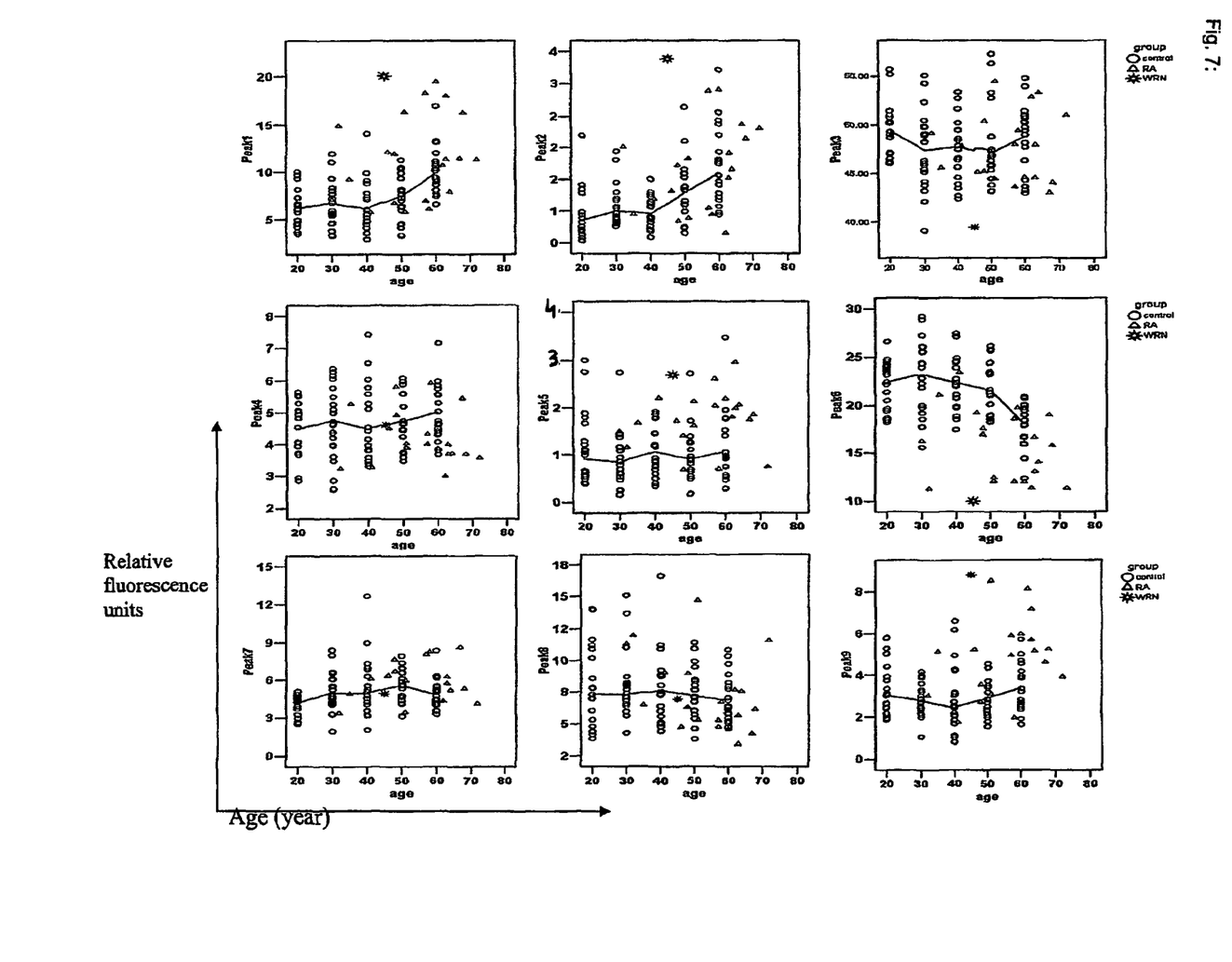
FIG. 7: Evolution of the N-glycan peaks in human serum in function of the age for rheumatoid arthritis patients (RA), Werner syndrome patients (WRN) and a male control group (CON)
Figure 8:
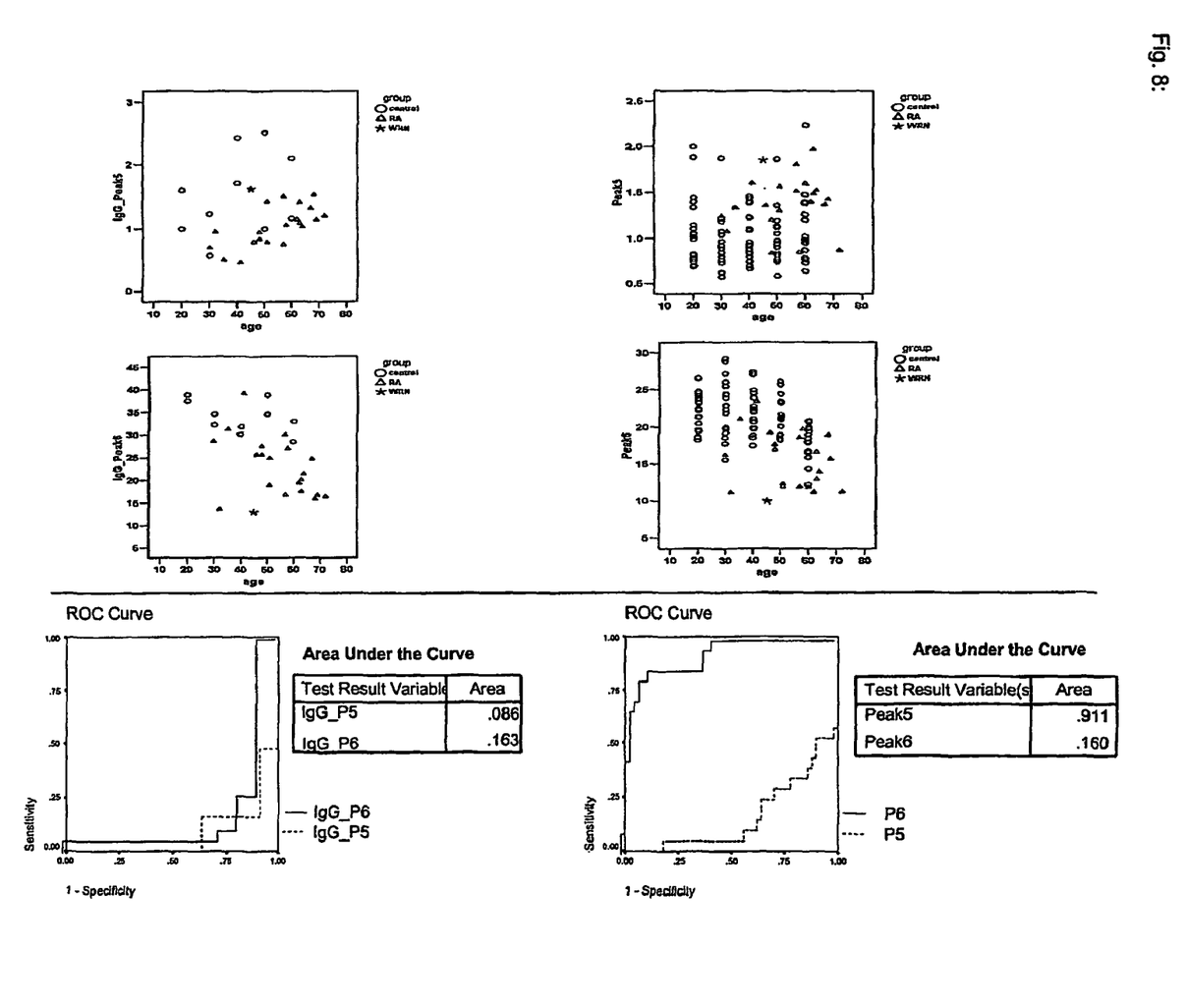
FIG. 8: Comparison between the N-glycan analysis of peak 5 and peak 6 of RA patients, WRN and male control. N-glycan analysis and ROC curve in total serum (left) and IgG (right).

Inflammation is a response of living tissue to mechanical, chemical or immunological challenge. Normal aging often results in the excessive production of autoimmune factors that destroy joint cartilage and other tissues in the body. Rheumatoid arthritis (RA) is an age-related disease that affects about 1% of the population worldwide. Abnormalities of both humoral and cellular immunity have been implicated in initiating and maintaining the chronicity of inflammation in this disease. Glycosylation changes, especially increased nongalactosylation and reduced α-1,6-linked core fucose on IgG, have been well documented in RA (Axford of al., 1992; Gornik of al., 1999). The finding of interesting changes in the glycosylation states of serum IgG of patients with RA led to a heightened interest that generated an enormous volume of data suggesting that RA may be a dysregulated glycosylation disease. To provide new insights into RA pathogenesis, we analyzed the N-glycan profiles of 20 RA patients, and compared them to reference profiles from healthy blood donors. As shown in FIG. 7, the concentrations of the sugar structures P5 and P6 are dramatically changed; the former is increased whereas the latter is decreased compared to healthy controls. The other peaks were similar to those in age-matched healthy controls. In the antibody fraction, however, a greater degree of alteration in the structure of sugars in RA disease was evidenced by decreases of P3, P4, P5 and P6, and an increase of P7 (FIG. 6). The means of variables P5 and P6 in RA cases were clearly different from those in controls, indicating a significant influence of RA on N-glycan parameters in total serum and IgG. These differences were evaluated by nonparametric Receiver Operating Curve (ROC) analysis. The result of ROC analysis indicates a classification efficiency, as measured by the Area Under the Curve (AUC), of 0.086 for P5 and 0.163 for P6 in the antibodies, and 0.911 for P5 and 0.160 for P6 in total serum (FIG. 8).

Example 4

N-Glycan Profiling in Werner Syndrome (WRN) Patients

Werner syndrome is an inherited disease characterized by the premature appearance of features of normal aging in young adults. The molecular role of WRN therefore remains to be proven, as does any role it might have in the aging process in general. To evaluate the relationship between Werner syndrome and aging, and to evaluate our aging biomarker, we analyzed the N-glycan profile from one WRN patient and compared it to those of the control groups. N-glycan profiling was perfumed on immunoglobulin (FIG. 6) and total serum (FIG. 7). As expected, the concentrations of several sugars in the patient were dramatically altered compared to age-matched controls, to an extent even greater than that in the old age group in this study (age 60 year). In total serum, P1, P2, P4 and P5 were increased, whereas P3 and P6 were decreased (FIG. 7). However, P1, P2, P3 and P6 in immunoglobulin and in serum displayed the same patterns of change (FIGS. 6 and 7). The change in immunoglobulin P4 was opposite to that seen in serum, but P5 was not altered. The changes observed in several peaks in WRN are consistent with those seen in the RA samples, indicating the value of N-glycan profiling as a general aging biomarker.

Example 5

Effect of Calorie Restriction on the Serum N-Glycan Profile in Mice and Rats

Numerous studies have established that caloric restriction (CR) is the most effective mechanism to lengthen life and to delay the onset of various age-related diseases in rodents by applying calorie restriction (CR) at 30-50% below ad libitum levels (Ingram et al., 2004; Cui et al., 2004). The basic mechanisms by which CR extends longevity and reduces susceptibility to diseases are not yet fully understood. In order to text biomarker of aging, the sera from mice and rats fed al libitum (AL) and a food restricted diet (CR) were analysis for N-glycan profiling.

Figure 9:
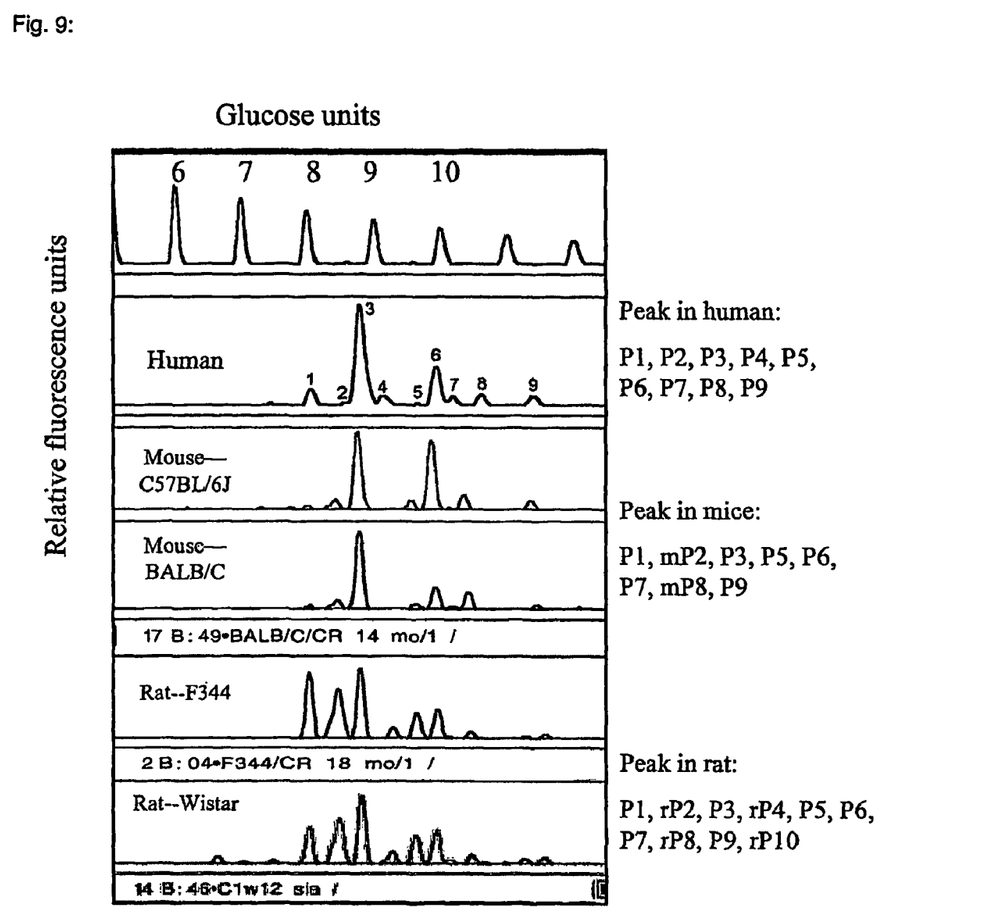
FIG. 9: Comparison N-glycan profile in serum among human, rat and mouse, indicating a species-specific N-glycan profiling pattern. The peak number corresponds to the number of N-glycan from human serum. The mice-specific N-glycan peaks are indicated as mP2 and mP8, whereas the rat-specific are rP2, rP4 and rP10.
Figure 10:
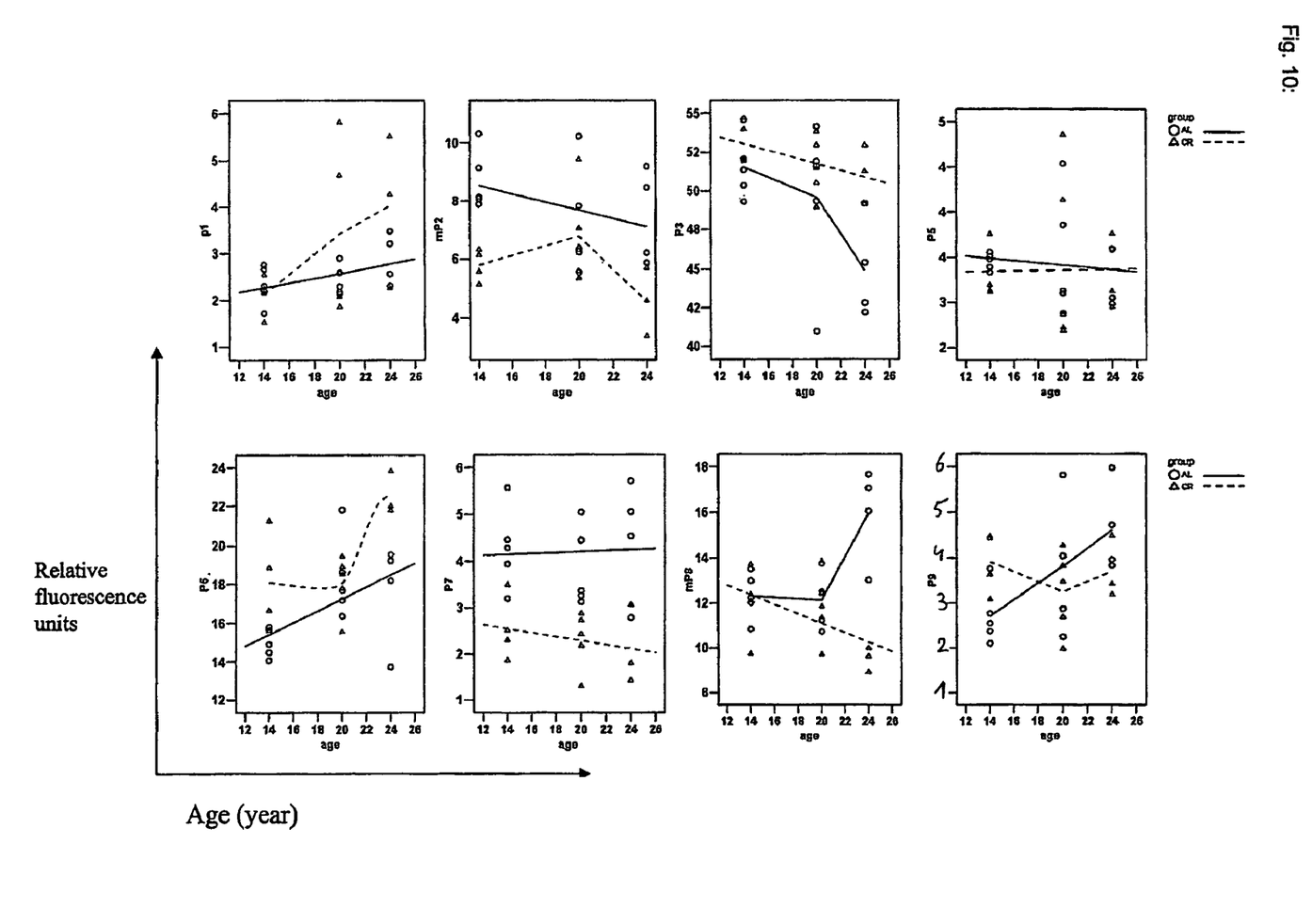
FIG. 10: Evolution of the N-glycan peaks in CR mice serum in function of the age.
Figure 11:
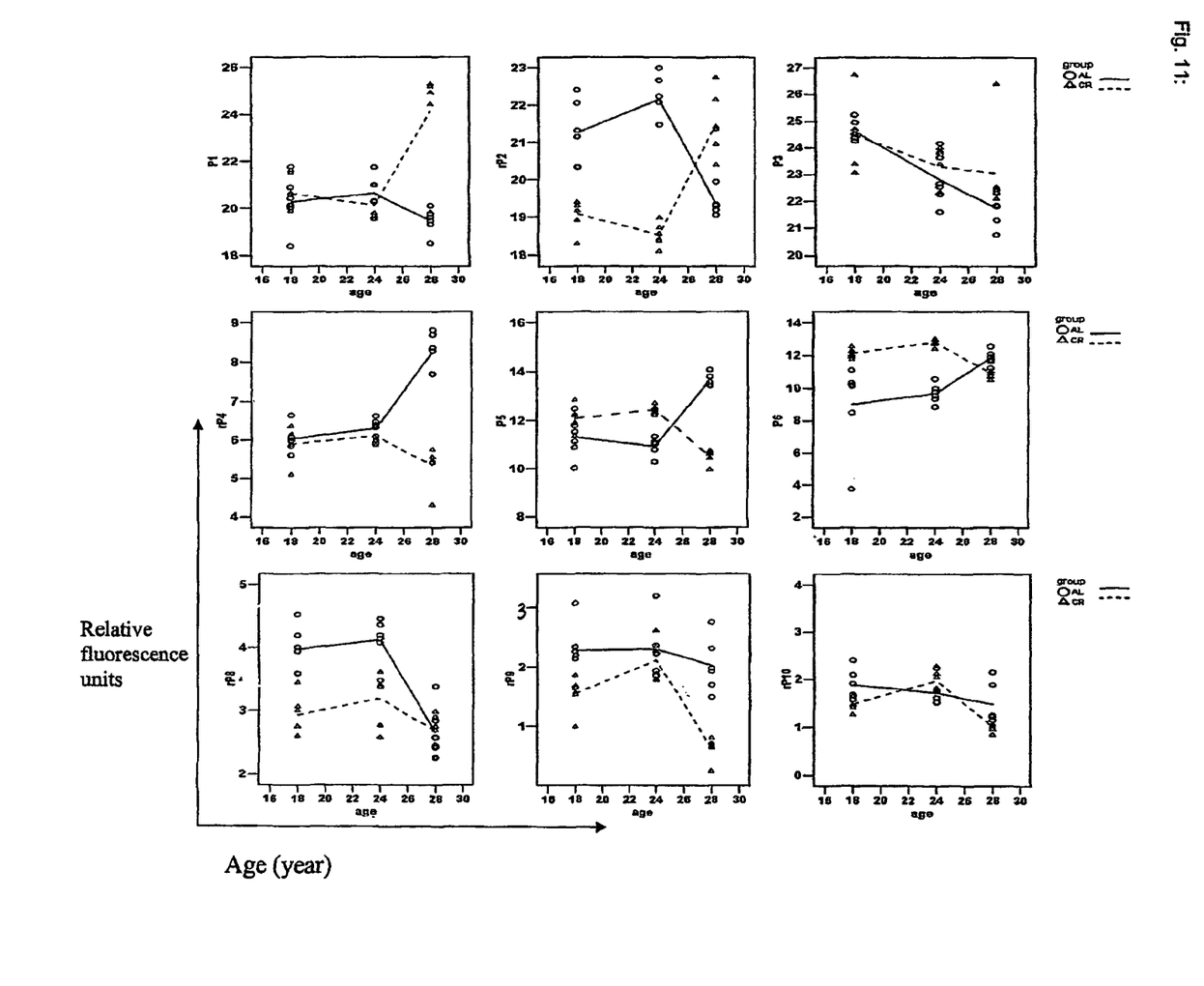
FIG. 11: Evolution of the N-glycan peaks in CR rat serum in function of the age.

Several sugar structures were found different from human and marked as either mice-specific or rat-specific peak (such as mP2 and mP8 in mice; rP2, rP4, rP8 and rP10 in rat), though they need further verified (FIG. 9). This observation is in agreement with the knowledge that N-linked sugar structures are species dependent. The N-glycan profile analyses were showed in FIG. 10 for CR mice and FIG. 11 for CR rat. We found that the trends of several peaks from CR animals differ or apart from AL animals. Moreover, the change of N-glycan concentration is also species-specific.

Example 6

Effect of CCl$_4$ Treatment on the Serum N-Glycan Profile of Rats

The repeated administration of CCl4 is widely employed as an animal model of human hepatic fibrosis/cirrhosis. In order to evaluate whether the sugar marker has high predictive values for the liver damage, we tested N-glycan profiling on the CCl4 treated, co-treated with INF-γ and control rat groups (Wistar). Take into account that N-glycosylation in animals is species-specific, we therefore profiled the N-linked glycan to get a fingerprinting in rat serum. A desialylated N-glycan profile on rats showed at least 10 major peaks (FIG. 9). N-glycan peaks of P1, P3, P5, P6, P7, P9 are consistent with that of human. However, four peaks (rP2, rP4, rP8 and rP10) are rat-specific N-linked sugars.

Figure 12:
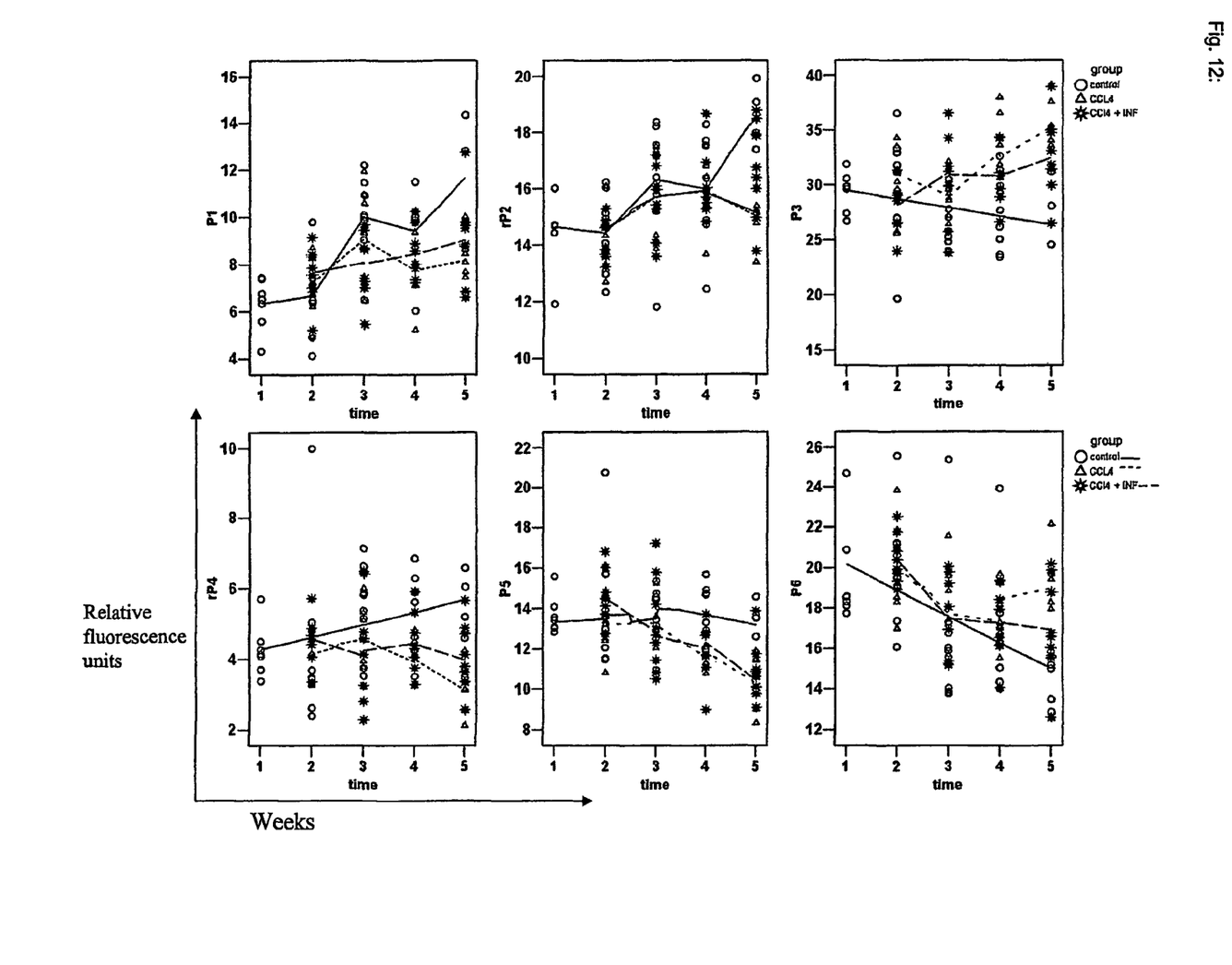
FIG. 12: N-glycan profile from rat sera treated with CCl4 and co-treated with Interferon-γ.

As shown in FIG. 12, six peaks reveled the changes of the trends either increased or decreased in the CCl4 treated rat group compare to the control group. The INF-γ group showed less slop changes than CCl4-group, indicating a protection of liver damage. The P7, rP8, P9 and rP10 in the CCl4 and INF groups revealed low fluorescence intensity and they consistent with control group.

Figure 13:
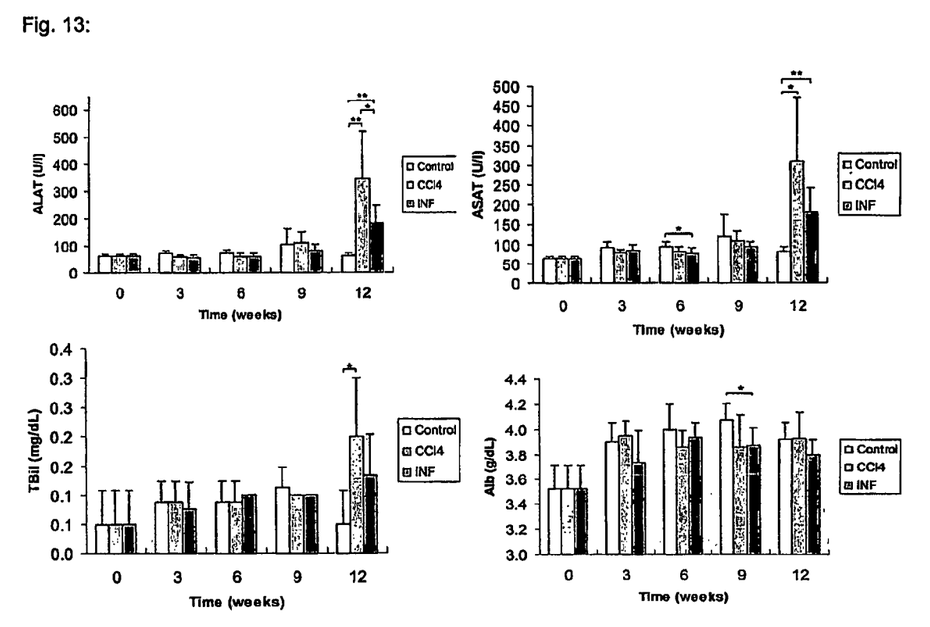
FIG. 13: Biochemical assay in serum from CCl4 exposed rat and Interferon-γ coeffect.

Moreover, the rat serum alanine aminotransferase activity (ALAT), aspartate aminotransferase activity (ASAT) and total bilirubin concentration (TBil) were analysed using routine photometric tests on a Hitachi 747 analyser (Boehringer Mannheim GmbH, Diagnostica) for subsequent assessment of hepatic injury and liver function, respectively. Surprisingly, the levels of liver enzymes ALAT, ASAT and bilirubin were significantly raised at Week 12 after administration of CCl4 (FIG. 13). It also showed that the liver damage causing by CCL4 treatment was partially protected by the dose of INF-γ, as indicated decreasing levels of bilirubin, ALAT and ASAT at Week 12.

Taken together, N-glycan profile between CCl4 group and control group showed different trends at stage Week 9, some peaks (P4 and P5) even in Week 6, whereas the biochemical test only revealed liver damage caused by CCl4 at a relatively later stage, Week 12. This result demonstrates more sensitivity of N-glycan test for cell cytotoxicity and liver damage than the biochemical test.

TABLE 1

| id | sex | age | RF |
|---|---|---|---|
| Ra 146 | v | 72 | n |
| Ra 248 | v | 32 | n |
| Ra 212 | m | 30 | n |
| Ra 226 | v | 51 | n |
| Ra 58 | v | 35 | n |
| Ra 61 | v | 57 | p |
| Ra 99 | m | 67 | p |
| Ra 117 | v | 48 | p |
| Ra 85 | v | 62 | p |
| Ra 147 | n | 48 | p |
| Ra 222 | v | 58 | p |
| Ra 105 | v | 63 | p |
| Ra 13 | v | 63 | p |
| Ra 3 | m | 51 | p |
| Ra 36 | m | 57 | p |
| Ra 37 | v | 41 | p |
| Ra 365 | m | 60 | p |
| Ra 325 | v | 68 | p |
| Ra 184 | v | 64 | p |
| Ra 53 | v | 46 | p |

RF: Rheumatoid factor.
RA patients provided by Dr. F. De Keyser, Afdeling Reumatologie, UZ

REFERENCES

Axford J S, Sumar N, Alavi A, Isenberg D A, Young A, Bodman K B, Roitt I M: Changes in normal glycosylation mechanisms in autoimmune rheumatic disease. J Clin Invest 1992; 89:1021-1031.

Callewaert N, Geysens S, Molemans F, Contreras R: Ultrasensitive profiling and sequencing of N-linked oligosaccharides using standard DNA-sequencing equipment. Glycobiology 2001; 11:275-281.

Cui Z, Willingham M C: The effect of aging on cellular immunity against cancer in SR/CR mice. Cancer Immunol Immunother 2004; 53:473-478

Guo Z, Mitchell-Raymundo F, Yang H, Ikeno Y, Nelson J, Diaz V, Richardson A, Reddick R: Dietary restriction reduces atherosclerosis and oxidative stress in the aorta of apolipoprotein E-deficient mice. Mech Ageing Dev 2002; 123:1121-1131

Ingram D K, Anson R M, de Cabo R, Mamczarz J, Zhu M, Mattison J, Lane M A, Roth G S: Development of calorie restriction mimetics as a prolongevity strategy. Ann N Y Acad Sci 2004; 1019:412-423.

The invention claimed is:

1. In a method of determining aging of a subject, the improvement comprising:
  analyzing a total serum N-glycan profile of the subject as a biomarker for aging.

2. In a method of determining aging of a subject, the improvement comprising:
  analyzing a serum N-glycan profile of the subject as a biomarker for aging, wherein said serum is free of IgG.

3. In a method of determining aging in a human, the improvement comprising:
  analyzing, in a sample taken from said human, agalacto N-glycans (peak 1 and 2) and galactosylated, fucosylated biantennary N-glycan (peak 6) as a biomarker for aging in human.

4. A method of testing the effect of administration of a consumable on an animal's virtual aging, said consumable selected from the group consisting of a medication, a chemical compound, food, diet, and any combination thereof, said method comprising:

determining a first serum N-glvcan profile of the animal,
administering the consumable to the animal,
determining a second serum N-glycan profile of the animal;
analyzing and comparing the first and second serum N-glycan profiles so as to test the effect of medication, a chemical compound, food and/or diet on the virtual age of an animal.

5. The method according to claim 4, wherein the consumable comprises chemical compounds.

6. A method for determining the virtual age of an animal, said method comprising:
a) obtaining a total serum sample from the animal;
b) releasing an N-glycan fraction from glycoproteins from the serum sample to form an N-glycan pattern;
c) analyzing the N-glycan pattern; and
d) determining the animal's virtual age by analyzing selected N-glycans representative for the virtual age of the animal species.

7. A method for determining the virtual age of an animal, said method comprising:
a) obtaining a serum sample from the animal;
b) removing the IgG from said serum sample;
c) releasing an N-glycan fraction from glycoproteins from the IgG free serum sample to form an N-glycan pattern;
c) analyzing the N-glycan pattern; and
d) determining the animal's virtual age by analyzing selected N-glycans representative for the virtual age of the animal species.

\* \* \* \* \*

UNITED STATES PATENT AND TRADEMARK OFFICE
CERTIFICATE OF CORRECTION

PATENT NO. : 7,993,822 B2  
APPLICATION NO. : 11/792203  
DATED : August 9, 2011  
INVENTOR(S) : Chen et al.

Page 1 of 1

It is certified that error appears in the above-identified patent and that said Letters Patent is hereby corrected as shown below:

In the claims:

| | | | |
|---|---|---|---|
| CLAIM 4, | COLUMN 9, | LINE 1, | change "N-glvcan" to --N-glycan-- |
| CLAIM 7, | COLUMN 10, | LINE 11, | change "c) analyzing" to --d) analyzing-- |
| CLAIM 7, | COLUMN 10, | LINE 12, | change "d) determining" to --e) determining-- |

Signed and Sealed this  
Twenty-eighth Day of January, 2014

Michelle K. Lee  
*Deputy Director of the United States Patent and Trademark Office*